(12) United States Patent
Ruymen et al.

(10) Patent No.: US 6,864,970 B1
(45) Date of Patent: Mar. 8, 2005

(54) APPARATUS AND METHOD FOR SCANNING PRODUCTS WITH A LIGHT BEAM TO DETECT AND REMOVE IMPURITIES OR IRREGULARITIES IN A CONVEYED STREAM OF THE PRODUCTS

(75) Inventors: Marc J. Ruymen, Korbeek-Lo (BE); Paul C. Berghmans, Zichem Brabant (BE)

(73) Assignee: Best N.V., Heverlee (BE)

( * ) Notice: Subject to any disclaimer, the term of this patent is extended or adjusted under 35 U.S.C. 154(b) by 551 days.

(21) Appl. No.: 09/686,581

(22) Filed: Oct. 11, 2000

(51) Int. Cl.$^7$ .............................................. G01N 21/00
(52) U.S. Cl. .................................................. 356/237.1
(58) Field of Search .......................... 356/237.1, 237.2, 356/239.4–239.6, 600–608; 250/221, 227.14, 227.16

(56) References Cited

U.S. PATENT DOCUMENTS

| | | | |
|---|---|---|---|
| 4,260,062 A | * 4/1981 | Lockett | 209/582 |
| 4,634,881 A | 1/1987 | Billion | |
| 4,723,659 A | 2/1988 | Billion | |
| 5,109,236 A | 4/1992 | Watanabe et al. | |
| 5,487,472 A | 1/1996 | Satake et al. | |
| 5,591,985 A | * 1/1997 | Tsuji et al. | 250/559.45 |
| 5,939,727 A | 8/1999 | Sommer | |
| 6,061,086 A | * 5/2000 | Reimer et al. | 348/125 |

FOREIGN PATENT DOCUMENTS

| | | |
|---|---|---|
| WO | 9831477 | 7/1998 |
| WO | 9844335 | 10/1998 |

OTHER PUBLICATIONS

PCT Search Report, Jan. 16, 2002.

* cited by examiner

*Primary Examiner*—Tu T. Nguyen
(74) *Attorney, Agent, or Firm*—Dority & Manning

(57) ABSTRACT

An apparatus for sorting products moving through a detection zone directs a light beam having a given cross sectional area towards a scanning zone through which the products move and are impinged upon by the light beam. A first detector is disposed to receive reflected light back from the products and has a first field of view larger than the light beam cross sectional area, the first detector being sensitive to substantially all of the direct and diffused reflected light from the products and generating a first signal corresponding thereto. A second detector also receives the reflected light and has a second field of view generally equal to the cross sectional area of the light beam. The second detector is sensitive to substantially only the direct reflected light from the products and generates a second signal corresponding thereto. Control circuitry causes a removal mechanism to remove impurities o products from the stream of products based on the signals from the first and second detectors individually or a difference between the signals.

32 Claims, 5 Drawing Sheets

APPARATUS AND METHOD FOR SCANNING PRODUCTS WITH A LIGHT BEAM TO DETECT AND REMOVE IMPURITIES OR IRREGULARITIES IN A CONVEYED STREAM OF THE PRODUCTS

BACKGROUND OF THE INVENTION

The present invention relates to an apparatus and a method for scanning any manner of conveyed products with a light beam, particularly a laser, in order to detect and remove impurities or irregular bodies in the stream of products.

Laser scanners or sorters are known in the art. For example, Belgian Electronic Sorting Technology (BEST) manufactures and markets (not in the U.S.) laser sorters identified as the LS9000 and the ARGUS. The LS9000 utilizes a combination of lasers to produce narrow beams of light to detect even slight variations between products according to their structure and/or color. Another company, Barco, manufactures and sells a line of laser sorting machines, including the ES6000i and ES VI720, advertised as capable of sorting products by color and texture. The fundamental principles of laser sorting technology are well known and understood by those skilled in the art.

U.S. Pat. Nos. 4,634,881 and 4,723,659 describe and claim embodiments of laser sorters. The '881 patent describes a device that utilizes a laser for directing a concentrated light beam in a scanning pattern through which translucent bodies are conveyed. A background device is spaced from the laser and is illuminated by a separate source of light independent of the laser beam. A receiver receives the light reflected from the background member and from the translucent bodies moving through the laser scanning beam, as well as the light from the independent light source that illuminates the background member. The receiver produces an output signal that changes when an impurity enters the concentrated scanning light beam. This signal is used to operate a device that removes the impurity from the stream of translucent bodies.

The '659 patent relates to a similar device and includes transport devices for moving a plurality of rows of translucent bodies, such as french cut potatoes, through the light beam. The transport devices are configured to move parallel rows of the translucent bodies simultaneously through the light beam path. The background element is not separately illuminated and is formed of a material that causes impinging light from the laser to be diffused within the background element in a manner similar to diffusion of the light in a translucent body. A receiver has a field of view larger than the cross-sectional area of the light beam and receives the light reflected from the background element and from the translucent bodies moving through the light beam. The receiver is made insensitive to light in the part of its field of view that corresponds with the point of impingement of the light beam on the translucent bodies. The receiver includes a photosensitive detector wherein the optical center point of the detector is made blind by means of a black spot so that the detector will not "see" the light reflected from the point of impingement of the laser beam on the translucent bodies. The patent describes that the detector may also receive reflected light from a mirror having a small hole defined therethrough that corresponds to the point of impingement of the laser beam on the translucent bodies. Thus, the reflected light from the point of impingement passes through the small hole in the mirror and is not reflected to the detector.

The present invention relates to an improvement upon the known systems and methods for sorting and scanning products with laser beams and provides distinct advantages over the conventional systems and methods.

OBJECTS AND SUMMARY OF THE INVENTION

It is a primary object of the principal invention to provide an improved laser sorting machine and method.

It is also a principal object of the present invention to provide a laser sorting machine and method that can sort various types of products by a combination of different signals so that the products can be sorted by color, structure, or a combination of color and structure.

Additional objects and advantages of the invention will be set forth in part in the following description, or may be obvious from the description, or may be learned through practice of the invention.

In accordance with the invention, an apparatus is provided for sorting products moving through a detection zone wherein it is desired to detect and remove irregularities or foreign objects from the product stream. The invention is not limited to use for any particular type of product, and is particularly useful for scanning food products, such as raisins, vegetables, nuts, shellfish, etc. The invention is useful in any application wherein irregular products or foreign objects in the product stream can be detected by texture and/or color differences.

The apparatus includes a light source, preferably at least one laser or a combination of lasers. The light source directs a concentrated light beam having a relatively small cross-sectional area towards a scanning zone. The products move through the scanning zone and are impinged upon by the light beam. The products can be conveyed or-propelled through the scanning zone by various devices. For example, in a "free-fall" configuration, the scanned products are allowed to "fall" from a vibrating or "shaker" table. The products free-fall essentially along their natural trajectory through the scanning zone. In an alternative embodiment, the products are propelled through the scanning zone in a "free-light" configuration wherein a conveyor moving at a relatively high speed propels the objects across the scanning zone.

The light reflected from the products includes light directly reflected from the point of impingement of the light beam on the products and light that is diffusely reflected from the area surrounding the impingement point due to diffusion or scattering of the light beam into the product. The degree of diffusion of the light into the product depends on the translucency of the product. For example, if the scanned body is a relatively non-translucent body (such as certain stones), relatively little light will be diffused into the product and substantially all of the reflected light is directly reflected from the point of impingement of the light beam on the product. On the other hand, if the scanned product is a relatively translucent body (such as certain food products), a large portion of the impinging light will diffuse into the translucent body and will be reflected as diffused or scattered light from the area surrounding the impingement point.

A plurality of different wavelength (color) light sources and detectors may be provided and utilized according to the desired sorting function. For example, specific visible color lasers and respective detectors may be provided for sorting the scanned objects by color alone. Other lasers (i.e. infrared) and respective detectors may be provided alone or in combination with the "color" detectors to sort by structure. Various combinations of detectors are withing the scope and spirit of the invention.

In one embodiment, a first detector is disposed to receive the light reflected back from the scanned products. The first detector has a field of view larger than the cross-sectional area of the light beam so as to be sensitive to substantially all of the direct and diffused reflected light from the products. This first detector generates a first signal corresponding to the received total (direct and diffused) reflected light.

A second detector is disposed to receive the reflected light back from the products. The second detector has a different ("second") field of view generally equal to the cross-sectional area of the light beam. In this way, the second detector is sensitive to substantially only the direct reflected light from the products and generates a second signal corresponding thereto.

Control circuitry is provided in operable communication with the first and second detectors to receive the first and second signals. The control circuitry generates control signals based on either of the signals individually or on a difference of the signals to sort the scanned products by any combination of color or texture depending on the exact signal or combination of signals used.

A beam splitter may be utilized upstream of the first and second detection devices. The beam splitter is disposed to split the reflected light from the products into a first beam directed to the first detector and a second beam directed to the second detector.

It may also be desired to utilize a device for "filtering" a portion of the reflected light from the detectors. For example, a polarizing beam splitter may be disposed between the scanning zone and the detection devices. The polarizing beam splitter cross-polarizes the reflected light received from the products with respect to a given polarization of the incident light beam and directs this cross-polarized light to the detectors. The reflected light received from the products having the same polarization as the light beam generally does not contain useful information and will pass through the beam splitter and be directed away from the detectors.

The first and second detector configuration may be utilized with a laser to sort by structure alone, or in combination with other wavelength lasers and respective detectors to provide additional color sorting capabilities. The first and second detector configuration may also be utilized to sort by color as well as structure, as discussed in greater detail herein. It should be appreciated that any combination of lasers, mirrors, focusing lenses, and beam splitters may be configured to analyze the reflected light beam by a number of different detector types to sort by color and/or structure.

The apparatus also preferably includes a removal mechanism, such as a bank of air ejectors disposed generally across the scanning zone, controlled by the control circuitry and acting in response to the control signals to remove unwanted objects or irregularities from the scanned products. For example, in the embodiment wherein the removal mechanism comprises a bank of air ejectors, the air ejectors are of a number and location so as to be able to remove an object from the products from anywhere across the width of the light beam scanning zone.

The scanning zone may be defined by a rotating multi-faceted mirror disposed between the light source and the scanning zone. The mirror directs the light beam in a high speed scanning pattern that defines the width of the scanning zone.

The apparatus and method according to the invention will be described in greater detail below through use of the appended figures.

DETAILED DESCRIPTION

Figure 1:
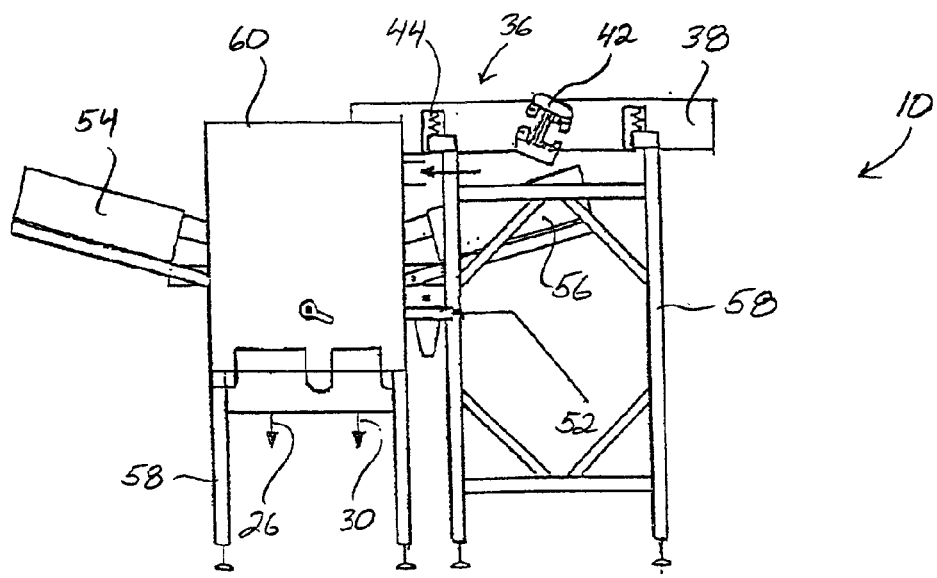
FIG. 1 is a diagrammatic perspective view of a laser sorter according to the present invention.

Reference will now be made in detail to the presently preferred embodiments of the invention, one or more examples of which are illustrated in the drawings. Each example is provided by way of explanation of the invention, and not meant as a limitation of the invention. For example, features illustrated or described as part of one embodiment can be used on another embodiment to yield a still further embodiment. It is intended that the present application include such modifications and variations as come within the scope and spirit of the invention.

U.S. Pat. No. 4,634,881 and U.S. Pat. No. 4,723,659 are incorporated herein by reference in their entirety for all purposes.

The published PCT applications WO 98/31477 and WO 98/44335 relate to features and systems that may be utilized in the present invention and these published applications are incorporated herein by reference in their entirety for all purposes.

Figure 2:
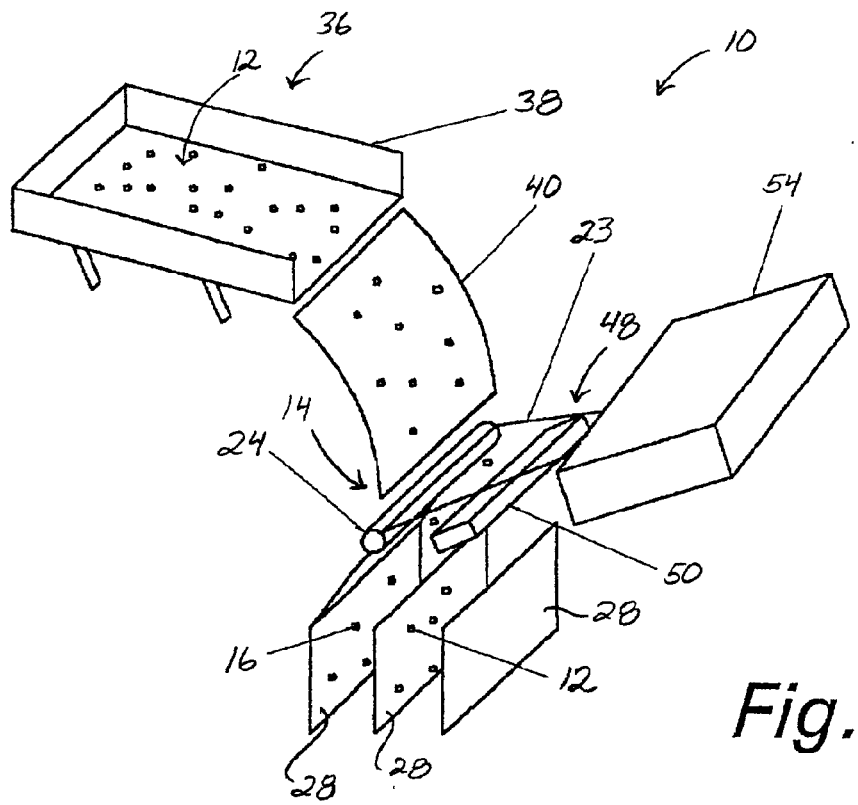
FIG. 2 is an operational illustration showing basic features of the laser sorter according to one embodiment of the invention.
Figure 3:
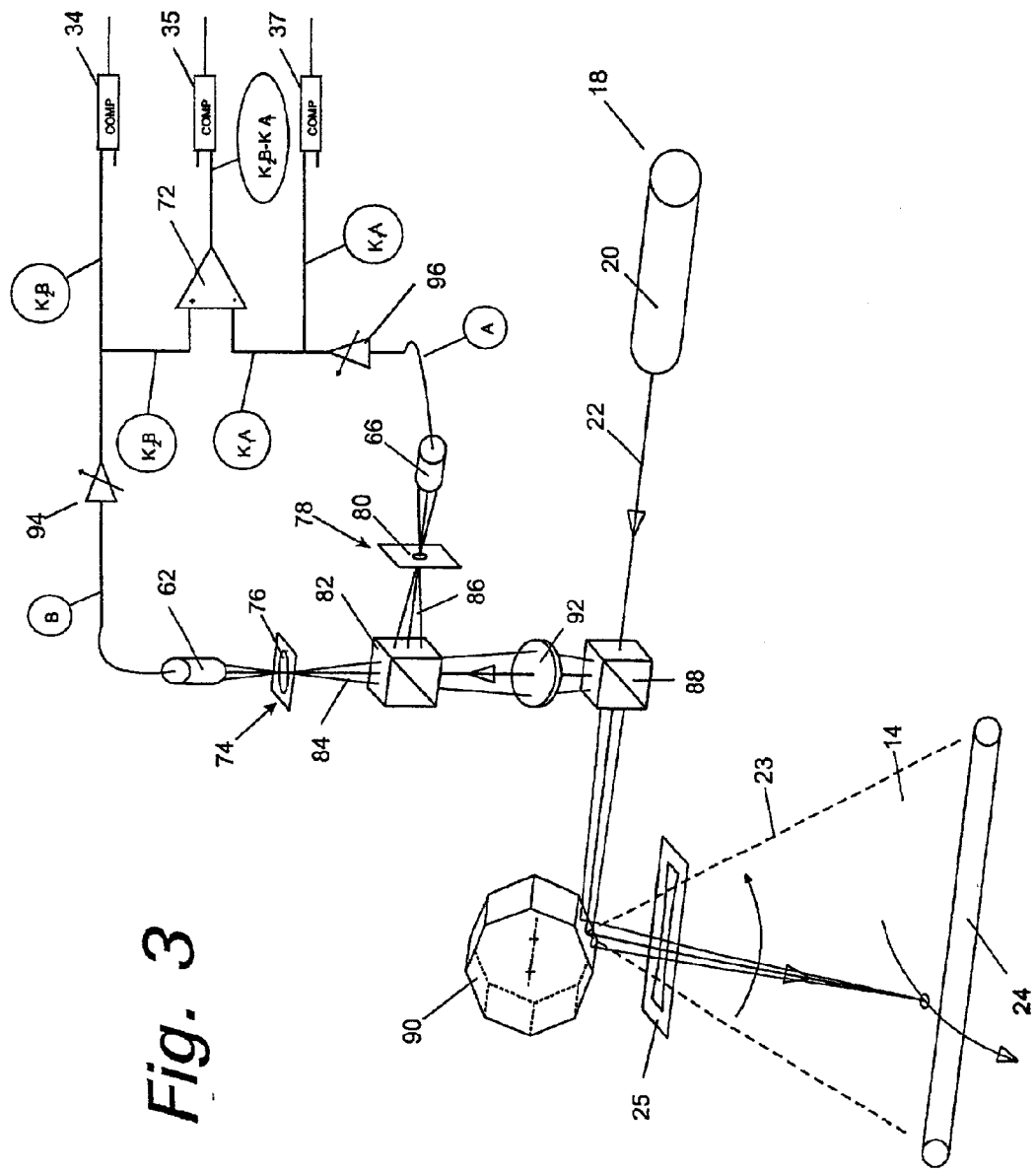
FIG. 3 illustrates the operating principles of the system according to the present invention.

Referring to FIGS. 1–3 in general, embodiments of an apparatus 10, particularly a laser sorter, according to the invention are illustrated. It should be appreciated that the apparatus 10 is not limited in its field of use, and has application in any environment wherein it is desired to detect and sort undesired or foreign bodies from a conveyed stream of products, or to sort products according to structural and/or color differences. Apparatus 10 is particularly useful in a food products processing environment wherein the use of laser sorters is well known.

FIGS. 1–3 illustrate the basic physical components of a laser sorter according to the invention. Apparatus 10 may include a cabinet 60 and frame members 58 for housing and supporting the various components. Frame members 58 and cabinet 60 can take on any manner of configuration to serve their intended purpose.

The optics packages 54, 56 are important features of the invention and will be described in detail below. In the embodiment illustrated, a front optics package 54 and a rear optics package 56 are provided to scan products 12 from two directions. However, one optics package and associated control circuitry are all that is necessary. Each optics package includes at least one light beam generating source 18, preferably at least one laser beam generator 20. Any combination of laser beam generators may be utilized depending on the intended scanning environment of apparatus 10. The number of lasers and their respective wavelength (color) depends on the application (color sorting and/or structure sorting) and products to be scanned. The light source (laser(s)) 20 produce a relatively narrow beam of light 22 with a single polarization, or a combination of these beams, to detect variations between products 12 according to their structure and/or color.

A transport device 36 is provided to convey a generally steady steam of products 12 through a detection or scanning zone 14 where the products are scanned by the light beam(s). In the embodiment illustrated in FIGS. 1–2, the transport device 36 includes a vibration or "shaker" table 38 mounted on springs 44 or other resilient devices. A vibrator 42 is incorporated with table 38 to impart a relatively constant "shaking" motion thereto to cause the products 12 to move randomly towards the distribution surface 40. The products are allowed to "free fall" off the edge of the table 38 and follow their natural trajectory due to gravity through the scanning zone 14.

It may be desired to provide a distribution surface 40 in the free-fall path. This surface 40 is a stationary member which is generally convex over at least a portion thereof in the direction of travel of products 12, the curvature of the convex portion being about equal to or slightly less than the free-fall path the products 12 will otherwise follow once they fall off of the end of table 38. The shape of surface 40 and the vibrating action of table 38 ensure that the products 12 leave the surface 40 and pass through the detection zone 14 in a single layer with substantially a thickness of only one product 12. A detailed explanation of distribution surface 40 is provided in the published PCT application WO 98/31477 incorporated herein.

Figure 2A:
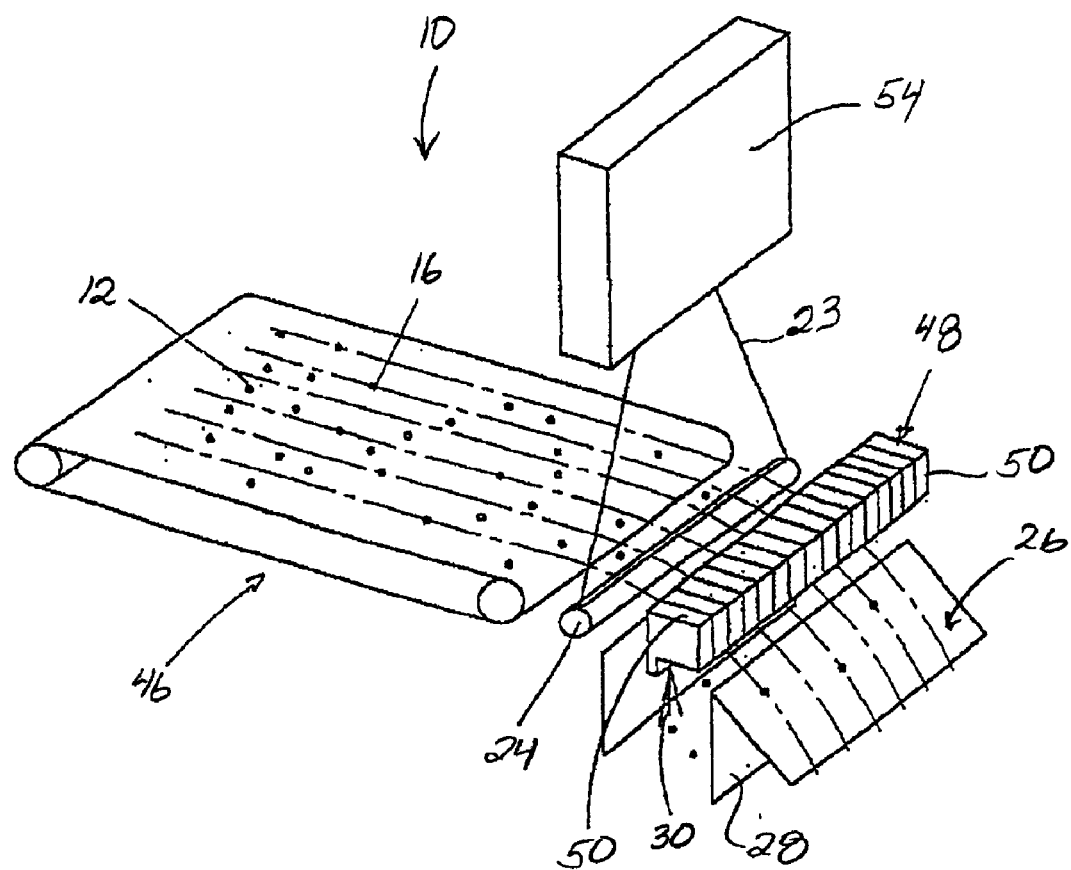
FIG. 2a is an operational view showing basic features of an alternative embodiment of the laser sorter according to the invention.

FIG. 2a illustrates an alternate embodiment wherein products 12 are conveyed along a conveyor 46 running at a speed so as to "propel" the products in "free-flight" across the detection zone 14. In this embodiment, the optics package 54 is positioned so that the products 12 travel through the scanning light beam as they travel along their "free-flight" trajectory.

The products pass through the scanning zone 14 where they are scanned from either one or both sides by any combination of lasers 20 (for example, three lasers per side) at a high scan rate, for example at a rate of up to 2,000 scans per second. As mentioned, the number of lasers 20 and their respective wavelengths (color) depends an the application and products to be scanned.

Immediately downstream of scanning zone 14, a removal device 48 is provided to remove detected foreign bodies or "reject" products 16 from the stream of products 12. In the illustrated embodiments, the removal device 48 is defined by a bank 50 of air ejection nozzles supplied by a source of compressed air (or other gas or fluid) 52. With this type of removal device, a plurality of adjacent air ejector nozzles are disposed below and across the scanning zone 14. As explained in grater detail below, if the control circuitry detects that a foreign body or irregular product has passed through the scanning zone, the air ejector nozzle(s) corresponding to the location of the foreign body or irregular product within the width of scanning zone 14 is actuated to emit a stream of relatively high pressure gas at a time determined by the control circuitry to correspond to the time at which the foreign body or irregular product passes by the air ejector nozzle(s), the relatively high pressure gas thereby impinging upon and deflecting the foreign body 16 into a reject chute 30. The "good" products 12 are allowed to follow their trajectory into an accept chute 26 for further processing. The chutes may be defined by any structure, for example by means of simple dividing plates 28.

The scanning and detection operation is illustrated conceptually in FIG. 3 It should be appreciated that the combination of elements shown in FIG. 3 is but an example of one embodiment of the invention. Those skilled in the art may devise other working configurations within the scope and spirit of the invention. Each laser 20 produces a concentrated beam 22 of light which passes through a polarizing beam splitter 88. If more than one laser is used, their respective light beams 22 may be combined in a dichroic mirror upstream from polarizing beam splitter 88 to produce one light beam 22 of different colors (wavelengths). The operating principles of a polarizing beam splitter are understood by those skilled in the art and a detailed explanation thereof is not necessary for purposes of the present description. In general, although laser light is already polarized, and although the polarization of the light beam 22 is oriented in such a way that it corresponds with the transmission polarization direction of the beam splitter, any irregularity or imperfection in the polarization of light beam 22 is removed as light beam 22 passes through the polarizing beam splitter 88. Light beam 22 leaving polarizing beam splitter 88 is directed to a high speed rotating polygon mirror 90.

The high speed polygon mirror 90 directs the light beam(s) in a scanning pattern 23 over the full width of the scanning zone 14 towards a reference or background element 24. It may be preferred to utilize a light gate 25 (FIG. 6) between the polygon mirror 90 and background element 24. This light gate 25 is described in detail in the published PCT application WO 98/44335 incorporated herein. In general, the light gate 25 ensures that the light reflected back to the detectors from the scanned bodies is "independent" of the position of the bodies in the scanning pattern of the light beam(s) 22. In this way, a substantially uniform sensitivity is obtained in scanning products across the full width of scanning pattern 23. The light gate 25 may be made in the form of a diaphragm having an opening that narrows in the direction of the point of greatest reflected light from the scanned bodies (generally in the middle of the scanning pattern 23). This opening is disposed in a plane perpendicular to the plane in which light beam 22 moves. The form and size of the diaphragm opening are chosen so that whenever the light beam 22 is directed towards the products, the signal generated by the detectors receiving the light "returned" by the scanned products is independent of the position of the products within the scanning pattern 23 of the light beam 22.

Background element 24 may be made of various materials depending on the type of objects to be scanned, and is preferably of a color and a translucency generally similar to the desired color and translucency of the particular product 12 being scanned. The products 12 to be scanned pass through scanning zone 14 between background element 24 and mirror 90.

In the scanning zone 14, the light beam(s) impact on the products 12 and a part of the light is reflected back to mirror 90 and polarizing beam splitter 88. The reflected light contains light having the same polarization as the incident light beam and light of perpendicular polarizations from the scanned bodies. The same polarized light is not particularly useful to the processing circuitry and may even mask certain useful information about the scanned products. Polarizing beam splitter 88 will split the reflected light into two polarization directions, one having the same polarization as the incident laser light, the polarization of which had been initially further aligned by the passage of the initial concentrated beam 22 of light from laser 20 through the same polarizing beam splitter 88, and the other having a 90 degree polarization (cross-polarized light) with respect to the incident laser light. The same polarized reflected light is passed directly through beam splitter 88 and is not further used. Thus, polarizing beam splitter 88 may be thought of as serving a "filtering" function in that it filters the same polarized light from the reflected light.

The cross polarized light from beam splitter 88 is directed to a focusing lens 92 and then to a non-polarizing beam splitter 82 (sometimes referred to in the art as a "50/50 beam splitter"). Beam splitter 82 passes about 50% of the cross polarized reflected light 84 to a first detector 62, and about 50% (86) to a second detector 66. The entire field of the cross polarized light is directed to both detectors 62,66 but at half of the magnitude or strength of the light passing through focusing lens 92.

Each of the detectors 62,66 have different field of views. First detector 62 has a field of view with a large enough diameter so that essentially all of the cross polarized light reflected from the scanned products, including the light diffused into translucent products (scattered light) and the relatively intense center light reflected from the point of impingement of the incident laser light on the product. The field of view of first detector 62 is defined by an upstream defining member 74, such as a plate or diaphragm member 76 having a relatively large aperture or hole defined therethrough with a diameter that thus defines the diameter of the field of view. First detector 62 produces a control signal "B" proportional to the entire reflected cross polarized light field. Signal "B" is passed to an adjustable gain op-amp 94 which produces an adjusted control signal "$K_2B$."

Second detector 66 has a field of view corresponding in size essentially to the cross-sectional diameter of the incident scanning light beam. Detector 66 thus senses only the relatively intense direct reflected light from the point of impact of the incident light beam on the products. The field of view of second detector 66 is defined by an upstream defining member 78, such as a plate or diaphragm member 80 having a hole or aperture defined therethrough with a diameter corresponding to the cross-sectional diameter of the incident laser light beam. Second detector 66 produces an output signal "A" proportional to the direct reflected light. Signal A" is passed to a second adjustable op-amp 96 which produces an adjusted control signal $K_1A$.

Figure 4:
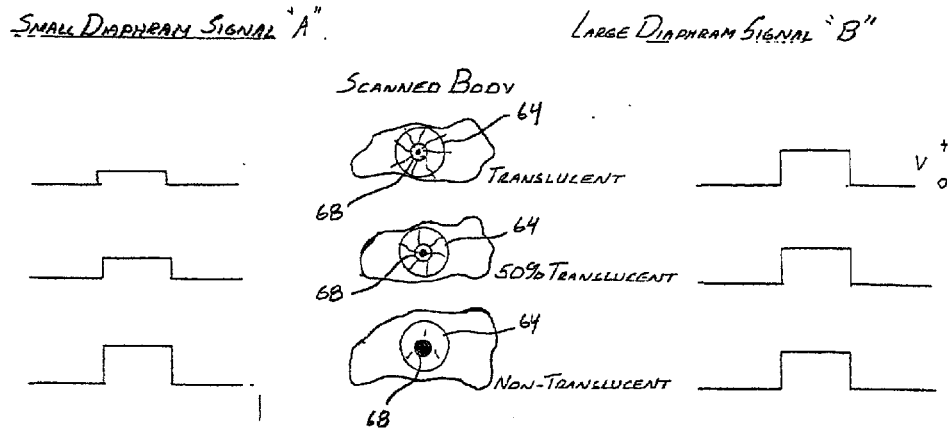
FIG. 4 is a sketch illustrating the principles of operation of the laser sorter according to the present invention.

FIG. 4 illustrates fundamental principles relating to the two detector configuration of FIG. 3. FIG. 4 shows three types of scanned bodies. The first body is a relatively translucent body. When the concentrated scanning light beam of a given diameter impinges upon the translucent body, the light will diffuse into the body. Circle 64 on the scanned bodies represents the field of view of the first sensor 62 (corresponds to the aperture size of the hole in diaphragm 76). This field is substantially larger than the circle 68, which corresponds to the field of view of second sensor 66. Thus, it should be appreciated that first sensor 62 is sensitive to substantially all of the light reflected from the body, including the diffused light and the direct light reflected from the point of impact of the scanning beam. The field of view 68 of the second sensor 66 has a diameter corresponding essentially to that of the impinging scanning light beam. The second sensor is thus sensitive only to the light reflected from the point of impingement of the laser beam on the body Referring to the first "translucent" body of FIG. 4, it can be seen that a substantial portion of the impinging light diffuses or scatters into the body. The signal strength for signal "A" is thus relatively small since only a relatively small amount of light is reflected directly back from the impingement point. The signal strength of signal "B" is relatively higher than signal "A" since the direct reflected light and diffused light are sensed, by first sensor 62.

The second scanned body in FIG. 4 is about 50% as translucent as the first body. Here, it can be seen that less light is diffused into the surrounding area of the body and more light is reflected directly back from the impingement point of the scanning beam. The strength of signal "A" is thus greater than that for the first translucent body. The strength of signal "B" is slightly higher than signal "A." The third body is a substantially non-translucent body, such as a stone, piece of plant stem, or other hard body. With this type of object, little if any light will diffuse into the body and the strength of signal "A" will be greatest. The strength of signal "B" will be about the same as signal "A" since sensor 62 will detect all of the direct reflected light.

Recognition of the principles shown in FIG. 4 and utilization of the signals A and B individually or the difference between signals A and B provides the present invention with the ability to sort scanned objects by color, structure (texture), or a combination of color and structure. For example, signal "B" is less structure dependent than signal "A" since the signal strength is generally the same regardless of the structure or texture of the scanned bodies. Thus, any change in the strength of signal "B" is a result of color effects, or "gray scale," of the scanned bodies. In other words a change in the strength of signal B would indicate that a body of a different color has been scanned as compared to the other scanned bodies. Thus, signal B may be used by the control circuitry 34 (FIG. 3) to sort/scan objects by color or gray scale only.

On the other hand, signal "A" is both color and structure dependent. As discussed above with respect to FIG. 4, for scanned objects of the same color, signal "A" will vary in strength depending on the translucency (structure or texture) of the bodies. For scanned bodies of the same structure (translucency), signal "A" will also vary depending on color changes of the bodies. For example signal "A" will be greater for a "white" scanned body as compared to a "brown" body having the identical structure. Signal "A" may thus be used by its associated control circuitry 37 to scan based on structure and color. Signal "A" is also useful in scanning for relatively small objects, for example pebbles or shells that are smaller than the field of view utilized to define "blind spots" utilized to define the field of view in certain prior art laser sorters, for example the sorter described in U.S. Pat. No. 4,723,659.

To sort based on the structure of the scanned bodies alone, the diffused light portion of signal "B" is "indirectly" determined from a difference of signals "A" and "B." This difference can be generated by, for example a conventional electronic signal differencing device or op-amp 72. Op-amp 72 electronically subtracts signal $K_1A$ corresponding to the direct reflected light from the impingement point of the scanning beam from signal $K_2B$ corresponding to the entire light field detected by sensor 62, so that the resulting signal corresponds essentially only to the diffused light portion of the reflected beam. This signal is passed to its associated control circuitry 35 to be acted upon by the air ejector nozzles.

Figure 5:
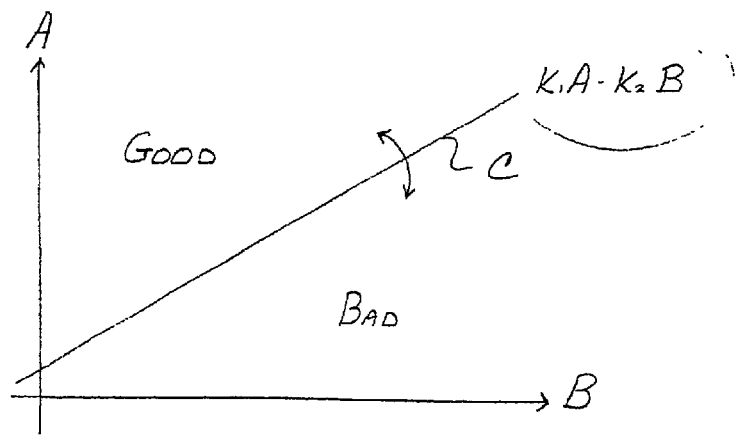
FIG. 5 is a diagram illustrating an operating principle of the present invention.

FIG. 5 represents a scanning principle of the invention based on the difference signal ($K_2B-K_1A$). Each of the signals "A" and "B" define an axis or the scanning limits of the system for scanning based on the difference signal from op-amp 72. The line "C" is defined by the difference signal and represents the threshold between "good" and "bad" scanned bodies. This threshold can be infinitely varied by adjusting the individual gain control op-amps 94,96 of the respective signals depending on the scanning environment and types of bodies to be scanned.

Thus, it should be appreciated that any combination of the three signals A, B, or C (difference signal) may be utilized by the control circuitry to actuate the air ejector nozzles when a foreign body or reject product is detected in the stream of scanned bodies. The fact that signals A and B are separately generated and processed allows the apparatus 10 according to the invention to perform advantageous sorting functions generally not possible with conventional laser sorters. Apparatus 10 can compensate for edge or shadow effects (as described in U.S. Pat. No. 4,634,881); can differentiate or sort by color; can detect and sort relatively small impurities or objects; has a relatively great degree of threshold detection adjustability or "fine tuning" because of the ability for separate gain control of signals A and B; and can reliably detect and sort glass and similar materials from scanned bodies.

Figure 6:
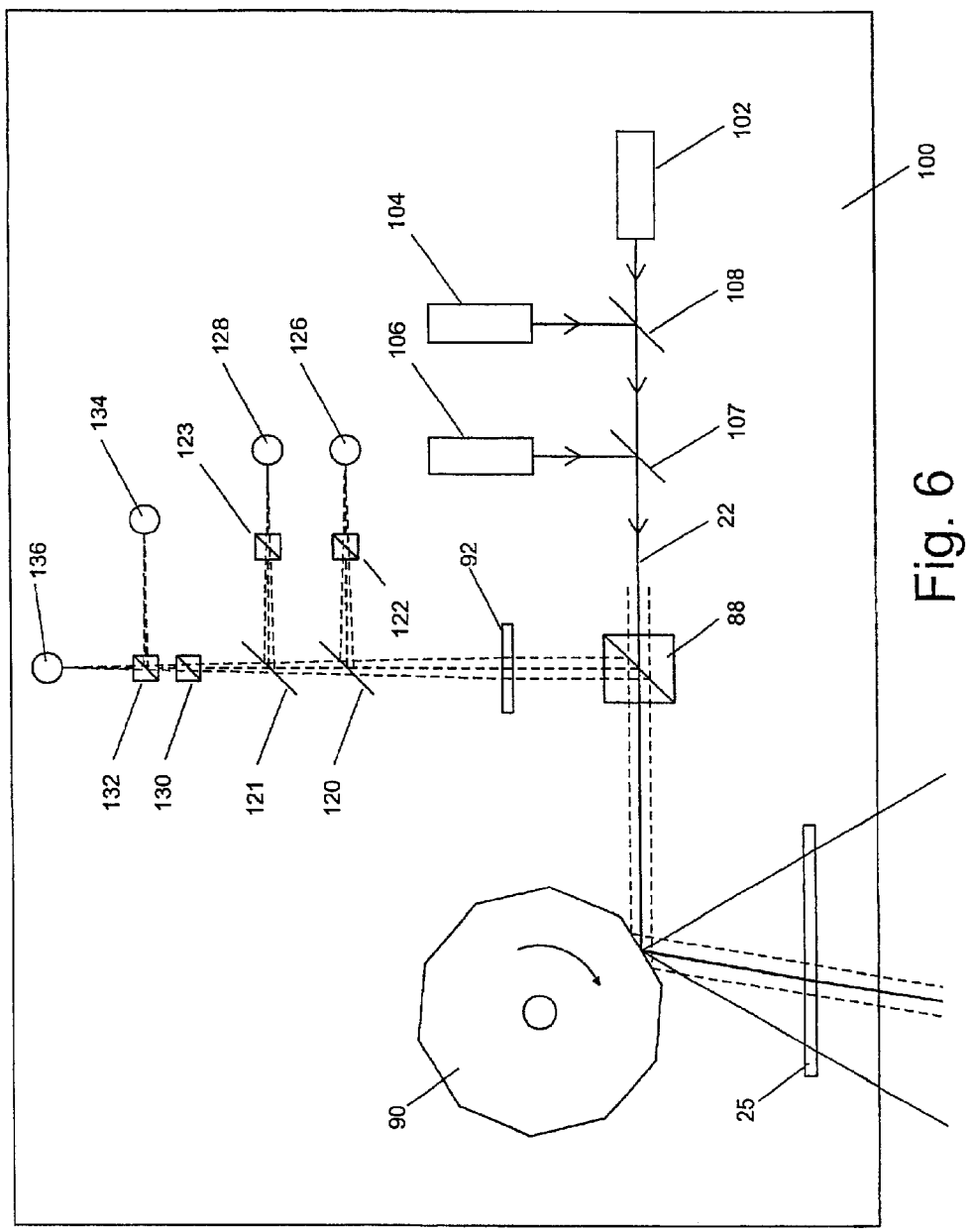
FIG. 6 is a diagrammatic view illustrating the components of an embodiment of the optics package according to the invention.

In certain applications, it may also be desired to sort by specific visible color variations in the scanned products by using a particular color laser and respective detector in addition to the detector configuration of FIG. 3. FIG. 6 is a diagrammatic and partial operational view of such an embodiment of an optics package 54 (56) according to the invention. The package components are preferably mounted on a relatively stiff and hard mounting board or member 100. This member 100 is in turn mounted within the respective optics package 54 (56). It should be appreciated that the components can be mounted on member 100 in virtually any pattern, and that any configuration or combination of mirrors or the like may be utilized to direct the light beam to the respective components. The present invention is not limited to any particular configuration of the components and the embodiment of FIG. 6 is presented as an example only.

In the embodiment of FIG. 6, an infrared laser 102, a red laser 104, and a green laser 106 are utilized. The green and red lasers are used to sort scanned objects by specific color, and the infrared laser is used to sort by structure. A dichroic mirror 108 combines the light from lasers 102 and 104 into a single light beam. This beam is combined with the beam from laser 106 by means of another dichroic mirror 107 into a single light beam 22. This beam 22 is directed to polarizing beam splitter 88. Polarizing beam splitter 88 refines/assures the polarization of the light beam 22, thereby guaranteeing that the discarded reflected light from the scanned bodies is only that light for which the polarization matched that of the incident beam. From the polarizing beam splitter 88, light beam 22 is directed to the rotating polygon mirror 90 and reflected by this rotating polygon mirror 90 through light gate 25 in its scanning patter across the scanning zone.

The light returned from the scanned products is represented in dashed lines in FIG. 6. A filtering device (not shown) may be used to filter out any ambient light or other unwanted light from the returned light. The return light is reflected from polygon mirror 90 to polarizing beam splitter 88. As discussed, the return light having the same polarization of the incident beam 22 is passed through polarizing beam splitter 88 and "discarded." The returned cross polarized light beam (compared to the incident light beam 22) is directed by a polarizing beam splitter mirror through a focusing lens 92 to a dichroic mirror 120. Dichroic mirror 120 reflects the returned cross polarized light of the green laser 106 and passes the returned cross polarized light of the red and infrared laser. The reflected light from dichroic mirror 120 passes through a polarizer 122 which refines/ assures the green light and is directed to a "green" light receiver 126. The light that passes dichroic mirror 120 is directed to another dichroic mirror 121 which reflects the returned cross polarized light from the red laser 104 and passes the returned cross polarized light from the infrared laser 102. The red light is directed through a polarizing beam splitter 123 to a "red" light receiver 128. The green and red light receivers produce signals proportional to the amount of green or red light they receive. By comparison with threshold values, these signals can thus be used to identify and sort the scanned bodies by color variations.

The light beam passed through dichroic mirror 121 is passed through a polarizer beam splitter 130 to a 50/50 beam splitter 132. About 50% of the light beam incident on beam splitter 132 is passed to small aperture receiver 134 and about 50% of the incident beam is passed to a large aperture receiver 136. These receivers are explained with reference to FIG. 3.

The configuration of FIG. 6 is particularly useful when an infrared laser is used as laser 102 for structure sorting capability. Although, as discussed above with respect to FIG. 3, the separate signals from receivers 134 and 136 can provide the capability to sort also by colors variations, in certain situations it may not be preferred to use infrared light for sorting by specific visible colors.

It should be appreciated by those skilled in the art that various modifications and variations can be made in the present invention without departing from the scope and spirit of the invention. For example, any combination of electronic components may be utilized to separately generate and process the individual signals A and B, or the difference signal C. It should also be appreciated that an optical set up which includes more focusing lenses, mirrors, and other optical devices to make the optical packages more compact and/or less sensitive to ambient light or other unwanted light is within the scope of the present invention. It is intended that the present invention include such modifications and variations as come within the scope of the appended claims and their equivalents.

What is claimed is:

1. An apparatus for detecting irregular or foreign objects in products moving through a scanning zone, said apparatus comprising:

a light source, said light source directing a concentrated light beam having a given cross sectional area in a scanning pattern towards a scanning zone wherein said products move through said scanning zone and are impinged upon by said light beam moving in said scanning pattern, said light being directly reflected from generally the impingement point of said light beam on said products and diffusely reflected from an area around said impingement point due to diffusion of said light beam into said products;

a first detector disposed to receive reflected light back from said products, said first detector having a first field of view larger than said light beam cross sectional area wherein said first detector is sensitive to substantially all of said direct and diffused reflected light from said products and generates a first signal corresponding thereto;

a second detector disposed to receive reflected light back from said products, said second detector having a second field of view generally equal to said cross sectional area of said light beam wherein said second detector is sensitive to substantially only said direct reflected light from said products and generates a second signal corresponding thereto; and control circuitry in operable communication with said first and second detectors to receive said first and second signals and generate control signals based on either of said signals individually or a difference of said signals.

2. The apparatus as in claim 1, further comprising a removal mechanism controlled by said control signals and configured to remove objects from said products in response thereto.

3. The apparatus as in claim 2, wherein said removal mechanism comprises a bank of air ejectors disposed generally across said scanning zone, said air ejectors being of a number and location so as to be able to remove an object from said products from anywhere across a width of said scanning zone.

4. The apparatus as in claim 1, wherein said control circuitry comprises a differencing device in receipt of said first and second signals, said differencing device generating a control signal from a difference of said first and second signals that corresponds essentially to only said diffuse reflected light.

5. The apparatus as in claim 1, further comprising a first defining member disposed operably before said first detector, said first defining member defining the size of said first field of view, and a second defining member disposed operably before said second detector, said second defining member defining the size of said second field of view.

6. The apparatus as in claim 5, wherein said first and second defining members comprise diaphragm devices having apertures therethrough of a size to define said first and second field of views respectively.

7. The apparatus as in claim 1, further comprising a beam splitter device disposed operably before said first and second detection devices, said beam splitter splitting reflected light from said products into a first split beam directed to said first detector and a second split beam directed to said second detector.

8. The apparatus as in claim 1, further comprising a polarizing beam splitter operably disposed between said scanning zone and said detection devices, said polarizing beam splitter cross polarizing reflected light received from said products with respect to a given polarization of said light beam and directing said cross polarized light to said detectors, and passing reflected light received from said products of a same polarization as said light beam away from said detectors.

9. The apparatus as in claim 8, wherein said polarizing beam splitter is disposed between said light source and said scanning zone so that said concentrated light beam of a given polarization passes through said polarizing beam splitter prior to impinging on said products.

10. The apparatus as in claim 1, further comprising a rotating multi-faceted mirror disposed between said light source and said scanning zone, said multi-faceted mirror directing said light beam in said scanning pattern across the width of said scanning zone.

11. The apparatus as in claim 1, wherein said light source comprises at least one laser beam generator.

12. The apparatus as in claim 1, wherein said light source comprises at least two laser beam generators, and said concentrated light beam comprises a combination of at least two laser beams of different wavelengths.

13. The apparatus as in claim 1, further comprising a vibrating table device disposed to receive said products and move said products towards said scanning zone, said scanning zone disposed below and adjacent to a forward edge of said vibrating table wherein said products substantially fall from said vibrating table and pass through said scanning zone in a free fall path.

14. An apparatus for sorting products moving through a detection zone wherein irregularities or foreign objects in the products are detected and removed, said apparatus comprising:

a light source, said light source directing a concentrated light beam having a given cross sectional area in -a scanning pattern towards a scanning zone wherein said products move in a mass through said scanning zone and are impinged upon by said light beam moving in said scanning pattern, said light being directly reflected from generally the impingement point of said light beam on said products and diffusely reflected from an area around said impingement point due to diffusion or scattering of said light beam into-said products;

a first detector disposed to receive reflected light back from said products, said first detector having a first field of view larger than said light beam cross sectional area wherein said first detector is sensitive to substantially all of said direct and diffused reflected light from said products and generates a first signal corresponding thereto;

a second detector disposed to receive reflected light back from said products, said second detector having a second field of view generally equal to said cross sectional area of said light beam wherein said second detector is sensitive to substantially only said direct reflected light from said products and generates a second signal corresponding thereto;

control circuitry in operable communication with said first and second detectors to receive said first and second signals and generate a first sorting control signal based on a difference between said first and second signals, said first sorting control signal corresponding substantially to only said diffused reflected light; and a plurality of air ejectors disposed below said scanning zone and extending across a path of movement of said mass of products, said air ejectors actuated by said control signal to remove unwanted objects from anywhere within said mass of products.

15. The apparatus as in claim 14, wherein said control circuitry is configured to generate additional sorting control signals dependent on said first and second signals individually, wherein said air ejectors are actuated by any one of said first sorting control signal and said additional sorting control signals.

16. The apparatus as in claim 15, comprising a first mode of sorting according to said first sorting control signal and based on structure of said products.

17. The apparatus as in claim 15, comprising a second mode of sorting according to an additional said sorting control signal dependent on said first signal and based on color variations of said products.

18. The apparatus as in claim 15, comprising a third mode of sorting according to an additional said sorting control signal dependent on said second signal and based on color variations and structure of said products.

19. The apparatus as in claim 14, further comprising a first defining member disposed operably before said first detector, said first defining member defining the size of said first field of view, and a second defining member disposed operably before said second detector, said second defining member defining the size of said second field of view.

20. The apparatus as in claim 14, wherein said first sorting control signal is used to sort by structure, and further comprising at least one additional visible light source and associated detector configured for sorting the scanned products by visible color differences.

21. A method for scanning and sorting a moving mass of products to remove unwanted irregularities and objects therefrom, said method comprising the steps of:

moving the mass of products through a scanning zone of a given width so that the products are essentially at single product depth as they pass through the scanning zone;

scanning a concentrated light beam across the path of the moving products in a scanning pattern so that all of the products are impinged by the light beam as they pass through the scanning zone, the light being directly reflected from generally the impingement point of the light beam on the products and diffusely reflected from an area around the impingement point due to diffusion or scattering of the light beam into the products;

splitting the reflected light from the products into two reflected beams;

receiving one of the reflected beams with a first detection device that is sensitive to substantially all of the reflected light from the products and generating a first signal proportional thereto;

receiving one of the reflected beams with a second detection device that is sensitive to substantially only the directly reflected light from the products and generating a second signal proportional thereto; and controlling a removal device to remove unwanted objects or irregularities from the mass of moving products with either of the first and second signals individually or a difference between the first and second signals.

22. The method as in claim 21, comprising sorting the mass of moving products based on structure of the products in a first sorting mode according to the difference between the first and second signals.

23. The method as in claim 21, comprising sorting the mass of moving products based on color of the products in a second sorting mode according to the first signal.

24. The method as in claim 21, comprising sorting the mass of moving products based on structure and color of the products in a third sorting mode according to the second signal.

25. The method as in claim 21, further comprising polarizing the reflected light beam back from the products and directing any reflected light of a same polarization of the incident light beam away from the detectors and directing only cross polarized light to the detectors.

26. The method as in claim 25, comprising polarizing the reflected light beam back from the products with a polarizing beam splitter device.

27. The method as in claim 21, comprising moving the mass of products essentially vertically through the scanning zone.

28. The method as in claim 27, comprising receiving the products in a vibrating table, moving the products to a forward edge of the vibrating table by the vibrating action of the vibrating table, and allowing the products to essentially fall from the forward edge of the vibrating table in a free fall trajectory through the scanning zone.

29. The method as in claim 28, further comprising allowing the product to fall in the free fall trajectory along a feed chute.

30. The method as in claim 21, further comprising scanning an additional concentrated light beam across the path of the moving products on an opposite side from the first light beam so as to scan opposite sides of the products.

31. The method as in claim 21, wherein said step of controlling a removal device comprises actuating any combination of a plurality of air ejectors disposed across the path of the mass of moving products.

32. The method as in claim 21, further comprising scanning the products with a visible light beam and receiving the visible reflected light with a respective detector that generates a signal proportional thereto, and using the signal to sort the product by specific visible light differences.

* * * * *